(12) United States Patent
Zhang et al.

(10) Patent No.: US 11,130,761 B2
(45) Date of Patent: Sep. 28, 2021

(54) SUBSTITUTED PYRROLO[2,1-F][1,2,4]TRIAZINES AS FGFR INHIBITORS

(71) Applicant: CSPC ZHONGQI PHARMACEUTICAL TECHNOLOGY (SHIJIAZHUANG) CO., LTD., Shijiazhuang (CN)

(72) Inventors: Yang Zhang, Shanghai (CN); Yikai Wang, Shanghai (CN); Linlin Chen, Shanghai (CN); Tao Feng, Shanghai (CN); Guoping Hu, Shanghai (CN); Jian Li, Shanghai (CN); Shuhui Chen, Shanghai (CN)

(73) Assignee: CSPC ZHONGQI PHARMACEUTICAL TECHNOLOGY (SHIJIAZHUANG) CO., LTD., Shijiazhuang (CN)

( * ) Notice: Subject to any disclaimer, the term of this patent is extended or adjusted under 35 U.S.C. 154(b) by 154 days.

(21) Appl. No.: 16/473,641

(22) PCT Filed: Dec. 28, 2017

(86) PCT No.: PCT/CN2017/119285
§ 371 (c)(1),
(2) Date: Sep. 23, 2019

(87) PCT Pub. No.: WO2018/121650
PCT Pub. Date: Jul. 5, 2018

(65) Prior Publication Data
US 2021/0130357 A1    May 6, 2021

(30) Foreign Application Priority Data
Dec. 29, 2016  (CN) .............................. 201611254119

(51) Int. Cl.
*A61K 31/53*        (2006.01)
*C07D 487/04*       (2006.01)

(52) U.S. Cl.
CPC ................. *C07D 487/04* (2013.01)

(58) Field of Classification Search
CPC .............................. A61K 31/53; C07D 487/04
USPC ........................................... 514/243; 544/83
See application file for complete search history.

(56) References Cited

U.S. PATENT DOCUMENTS

2016/0136168 A1    5/2016  Sootome

FOREIGN PATENT DOCUMENTS

| TW | 201536293 A | 10/2015 | |
|----|----|----|----|
| WO | 2015008844 A | 1/2015 | |
| WO | WO-2018121650 A1 * | 7/2018 | ........... A61K 31/519 |

OTHER PUBLICATIONS

Jordan, V. C. Nature Reviews: Drug Discovery, 2, 2003, 205.*
Hackam, et al. JAMA, 296(14), 2006, 1731-1732.*
Berge et al., "Pharmaceutical Salts", Journal of Pharmaceutical Science, 1977, vol. 66, p. 1-19.
Remington, The Science and Practice of Pharmacy, 21st Ed., Lippincott, Williams & Wilkins, 2005.
International Search Report and Written Opinion of PCT/CN2017/119285 dated Apr. 2, 2018.
Office Action dated Aug. 4, 2021 issued in counterpart Chinese application 201780081651.X.

* cited by examiner

*Primary Examiner* — Douglas M Willis
(74) *Attorney, Agent, or Firm* — SZDC Law PC

(57) ABSTRACT

Disclosed are an FGFR inhibitor and the use thereof in the preparation of a drug for treating FGFR-related diseases. In particular, disclosed are a compound as shown in formula (I) and a pharmaceutically acceptable salt thereof.

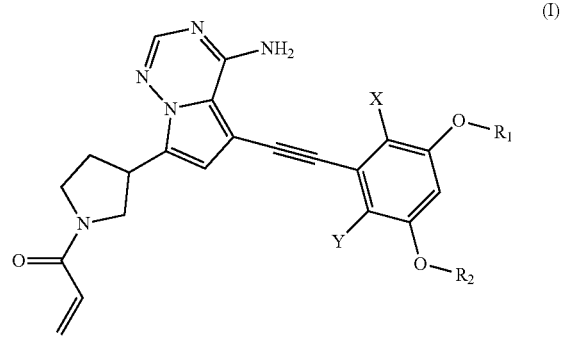

20 Claims, No Drawings

SUBSTITUTED PYRROLO[2,1-F][1,2,4]TRIAZINES AS FGFR INHIBITORS

CROSS-REFERENCE TO RELATED APPLICATIONS

The present application is the national stage application of PCT/CN2017/119285, filed on Dec. 28, 2017, which claims the benefit of the Chinese patent application No. 201611254119.7 filed to China National Intellectual Property Administration on Dec. 29, 2016, the contents of which are incorporated herein by reference in its entireties.

BACKGROUND OF THE INVENTION

Field of the Invention

The invention relates to an FGFR inhibitor and a use thereof in manufacturing a medicament for treating a disease associated with FGFR. Specifically, the invention relates to a compound of formula (I) and a pharmaceutically acceptable salt thereof.

Description of Related Art

The fibroblast growth factor receptor (FGFR) is a receptor for fibroblast growth factor (FGF) signaling consisting of four members (FGFR1, FGFR2, FGFR3, FGFR4). It is a glycoprotein composed of an extracellular immunoglobulins (Ig) domain, a hydrophobic transmembrane region and an intracellular portion of a tyrosine kinase domain. Fibroblast growth factor (FGF) plays an important role in many physiological regulatory processes such as cell proliferation, cell differentiation, cell migration, and angiogenesis via these receptors (FGFR). There is a lot of evidence showing that the abnormalities of FGF signaling pathway (e.g., high expression, gene amplification, gene mutation, chromosome recombination) are directly related to many pathological processes such as tumor cell proliferation, migration, invasion and angiogenesis. Therefore, FGFR has become an important therapeutic target attracting extensive interests.

Therefore, there is a need for novel compounds and methods for inhibiting FGFR to treat proliferative diseases such as cancer. The invention satisfies this need.

WO2015008844 discloses a series of compounds having an inhibitory activity on FGFR, including reference compound 1.

BRIEF SUMMARY OF THE INVENTION

The invention provides a compound of formula (I) or a pharmaceutically acceptable salt thereof,

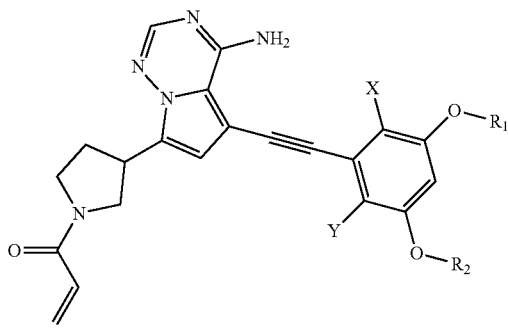

(I)

wherein

X and Y are independently H, F, Cl, Br or I;

$R_1$ is $C_{1-3}$ alkyl;

$R_2$ is $C_{1-3}$ alkyl.

In some embodiments of the invention, $R_1$ is Me or Et.

In some embodiments of the invention, $R_2$ is Me or Et.

In some embodiments of the invention, X is H, Y is H.

In some embodiments of the invention, X is F, Y is F.

In some embodiments of the invention, X is Cl, Y is Cl.

In some embodiments of the invention, $R_1$ is Me or Et, other variables are as defined above.

In some embodiments of the invention, $R_2$ is Me or Et, other variables are as defined above.

In some embodiments of the invention, X is H, Y is H, other variables are as defined above.

In some embodiments of the invention, X is F, Y is F, other variables are as defined above.

In some embodiments of the invention, X is Cl, Y is Cl, other variables are as defined above.

In some embodiments of the invention, the compound or the pharmaceutically acceptable salt thereof, which is

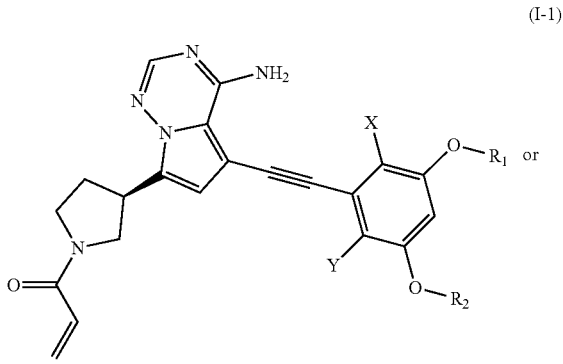

(I-1)

or

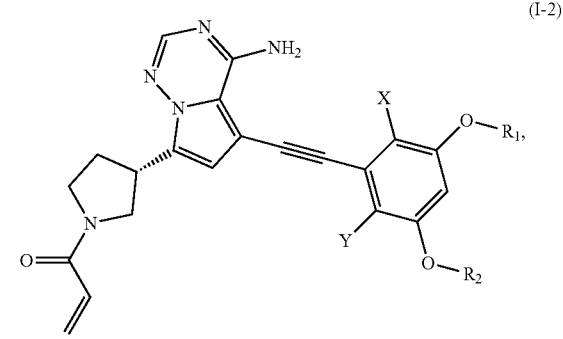

(I-2)

wherein, X, Y, $R_1$ and $R_2$ are as defined herein.

Other embodiments of the invention can be obtained by arbitrarily combining the above variables.

The invention also provides a compound or a pharmaceutically acceptable salt thereof, which is selected from the group consisting of

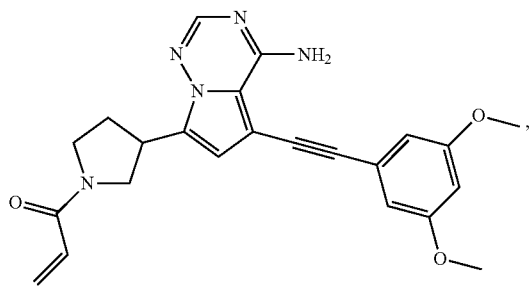

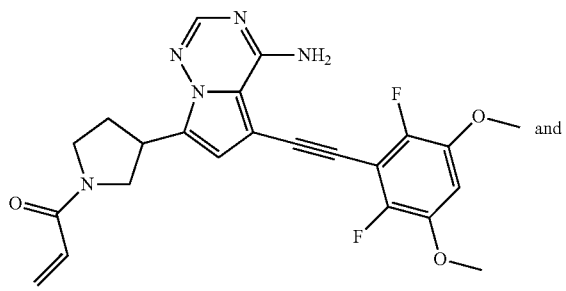

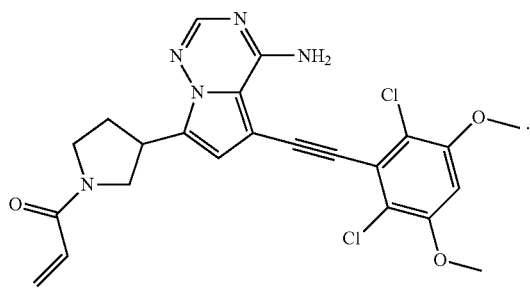

The invention also provides a compound or a pharmaceutically acceptable salt thereof, which is selected from the group consisting of

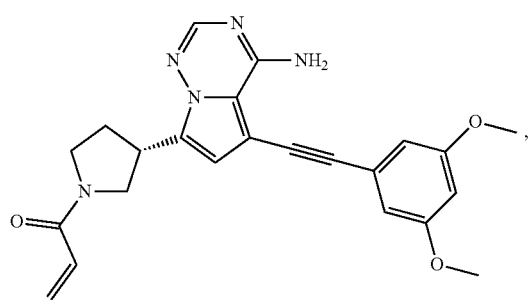

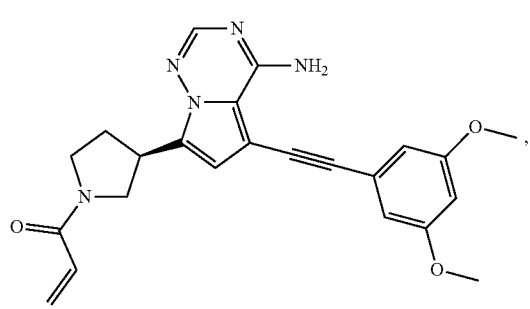

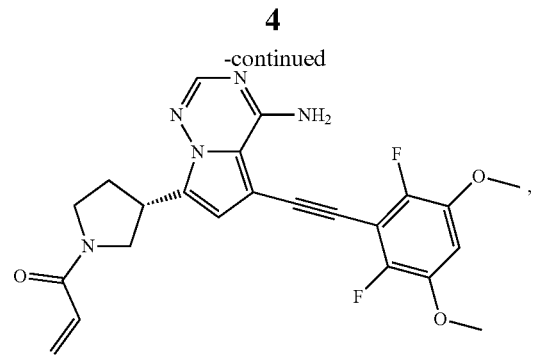

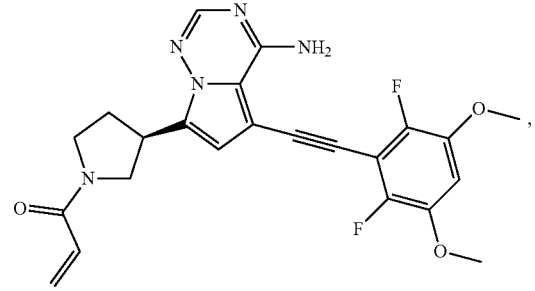

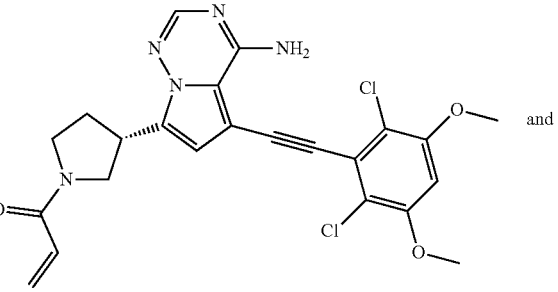

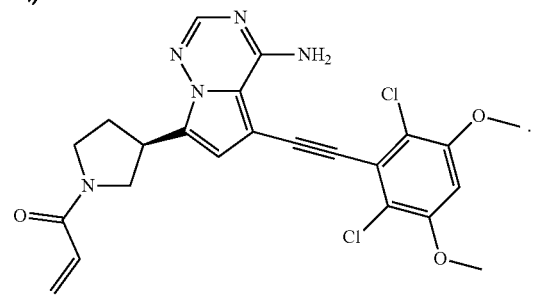

The invention also provides a pharmaceutical composition comprising a therapeutically effective amount of the compound or the pharmaceutically acceptable salt thereof, and a pharmaceutically acceptable carrier.

The invention also provides a use of the compound or the pharmaceutically acceptable salt thereof, or the composition in manufacturing a medicament for treating a disease associated with FGFR.

The invention also provides a use of the compound or the pharmaceutically acceptable salt thereof, or the composition in manufacturing a medicament for treating a disease associated with FGFR.

In some embodiments of the invention, the use, wherein the disease associated with FGFR is a solid tumor caused by FGFR mutation or overexpression, including but not limited to gastric cancer, hepatocellular carcinoma, intrahepatic cholangiocarcinoma, etc.

In some embodiments of the invention, the use, wherein the disease associated with FGFR is gastric cancer, hepatocellular carcinoma or intrahepatic cholangiocarcinoma, each of which is caused by FGFR mutation or overexpression.

Technical Effects

Some compounds of the invention exhibit a picomolar-level inhibitory activity on FGFR1 and FGFR4, and some compounds exhibit a comparable inhibitory activity against FGFR4 and FGFR1.

Definition

Unless otherwise specified, the following terms and phrases used herein are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the invention that is prepared by reacting the compound having a specific substituent of the invention with a relatively non-toxic acid or base. When the compound of the invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (e.e., arginine and the like), and a salt of an organic acid such as glucuronic acid and the like (refer to Berge et al., "*Pharmaceutical Salts*", *Journal of Pharmaceutical Science* 66: 1-19 (1977)). Certain specific compounds of the invention that contain both basic and acidic functional groups can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the invention also exists in prodrug form. The prodrug of the compound described herein is the compound that readily undergoes chemical change under physiological condition to be converted into the compound of the invention. Additionally, the prodrug can be converted to the compound of the invention by a chemical or biochemical method in vivo environment.

Certain compounds of the invention can exist in an unsolvated form or a solvated form, including hydrated form. Generally, the solvated form is equivalent to the unsolvated form, and both are encompassed within the scope of the invention.

Certain compounds of the invention can have an asymmetric carbon atom (optical center) or a double bond. The racemate, diastereomer, geometric isomer and individual isomer are all encompassed within the scope of the invention.

Unless otherwise specified, the absolute configuration of a stereogenic center is represented by a wedged bond and a dashed bond (   ), a wavy line (  ) represents a wedged bond or a dashed bond (  or  ). When the compound described herein contains an olefinic double bond or other geometric asymmetric centers, E and Z geometric isomers are included unless otherwise specified. Likewise, all tautomeric forms are encompassed within the scope of the invention.

The compound of the invention may have a specific geometric or stereoisomeric form. The invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the invention. The substituent such as alkyl may have an additional asymmetric carbon atom. All these isomers and mixtures thereof are encompassed within the scope of the invention.

Optically active (R)- and (S)-isomer, or D and L isomer can be prepared using chiral synthesis or chiral reagents or other conventional techniques. If one kind of enantiomer of certain compound of the invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compound of the invention may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). All isotopic variations of the compound of the invention, whether radioactive or not, are encompassed within the scope of the invention.

The term "pharmaceutically acceptable carrier" refers to any agent or carrier medium which is capable of delivering an effective amount of the active substance of the invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field. The additional information about the carrier can be referred to *Remington: The Science and Practice of Pharmacy*, 21st Ed, Lippincott, Williams & Wilkins (2005), the disclosure of which is incorporated herein by reference.

The term "excipient" generally refers to a carrier, a diluent and/or a medium required for formulating an effective pharmaceutical composition.

For a medicament or a pharmacologically active agent, the term "effective amount" or "therapeutically effective amount" refers to a nontoxic but sufficient amount to achieve a desired effect of the medicament or the agent. For the oral dosage form of the invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

Unless otherwise specified, the term "alkyl" refers to a linear chain or branched saturated hydrocarbon group, can be mono-substituted (e.g. —CH$_2$F) or poly-substituted (e.g. —CF$_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo(C$_1$-C$_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The compound of the invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the invention.

All of the solvents used by the invention are commercially available. The invention employs the following abbreviations: eq represents equivalent or equal; DMSO represents dimethyl sulfoxide.

Compounds are named manually or by ChemDraw® software, the commercially available compounds use their vendor directory names.

DETAILED DESCRIPTION OF THE INVENTION

The invention will be specifically described below by way of embodiments, but the scope of the invention is not limited thereto. While the invention has been described in detail and with reference to specific embodiments thereof, it will be apparent to the skilled in the art that various changes and modifications can be made therein without departing from the spirit and scope thereof.

Reference Embodiment 1: WXR1

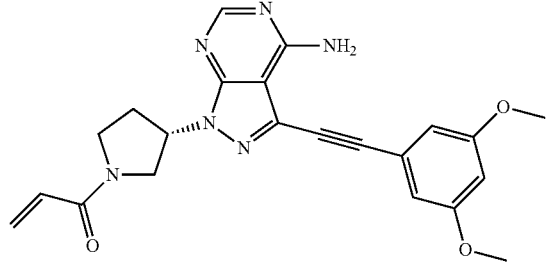 [SMILES: C=CC(=O)N1CC[C@H](n2nc(C#Cc3cc(OC)cc(OC)c3)c3c(N)ncnc32)C1]

Compound WXR1 was synthesized according to the route disclosed by WO2015008844. $^1$H NMR (400 MHz, DMSO-$d_6$) δ 8.40 (d, J=3.0 Hz, 1H), 6.93 (d, J=2.5 Hz, 2H), 6.74-6.52 (m, 2H), 6.20-6.16 (m, 1H), 5.74-5.69 (m, 1H), 5.45-5.61 (m, 1H), 4.12-3.90 (m, 2H), 3.90-3.79 (m, 8H), 2.47-2.30 (m, 2H). MS m z: 419.1 [M+H]$^+$.

Intermediate A1:

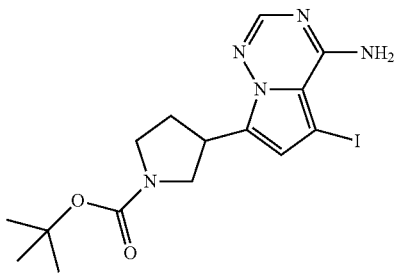 [SMILES: CC(C)(C)OC(=O)N1CCC(c2cc(I)c3c(N)ncnn23)C1]

Synthetic Route:

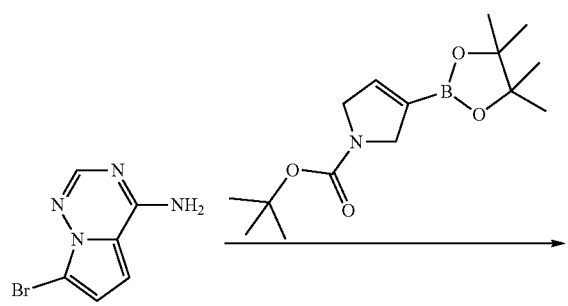

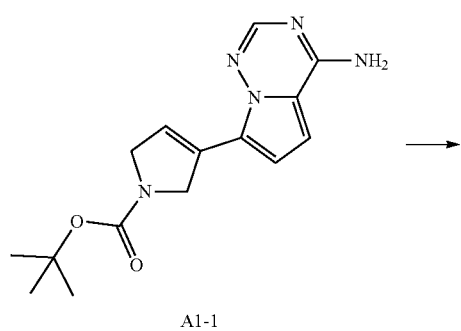

A1-1

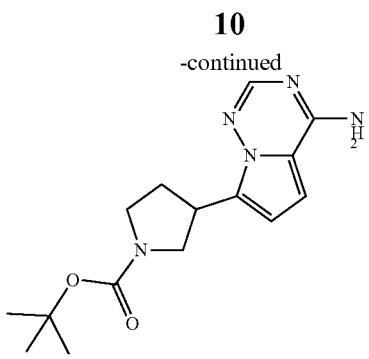

A1-2

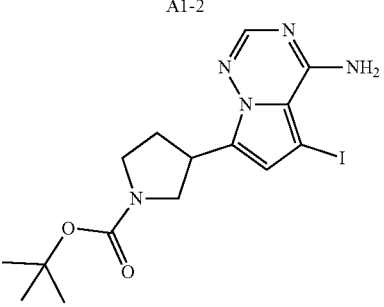

A1

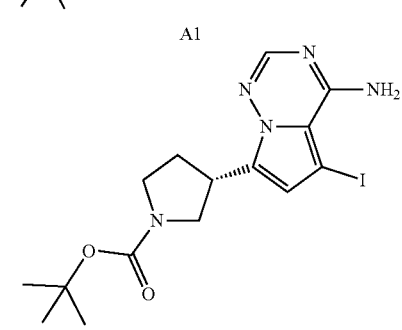

A1-A or A1-B

+

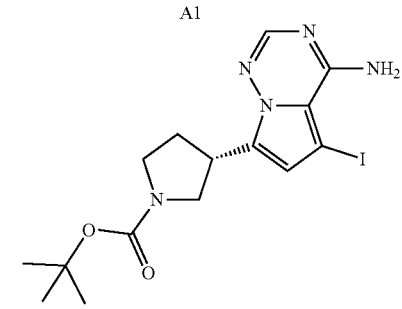

A1-A or A1-B

Step 1: Synthesis of Compound A1-1

4-Amino-7-bromopyrrolo[2,1-f][1,2,4]triazine (3.00 g, 14.1 mmol, 1.00 eq) was dissolved in a mixed solvent of 1,4-dioxane (40 mL) and water (8 mL) at room temperature, followed by successive addition of N-Boc-2,5-dihydro-1H-pyrrole-1-boronic acid pinacol ester (4.36 g, 14.8 mmol, 1.05 eq), potassium phosphate (8.97 g, 42.2 mmol, 3.00 eq) and 1,1'-bis(diphenylphosphino)ferrocene chloropalladium (1.03 g, 1.41 mmol, 0.10 eq). The reaction solution was heated to 80° C. under nitrogen atmosphere and stirred for 2 hours. After completion of the reaction, the reaction solution was cooled to 25° C. and poured into 20 mL water. A black solid was generated, collected by filtration, and then dissolved in a mixed solvent of dichloromethane/methanol (100 mL, 5/1). The mixture was filtered again, then the filtrate was dried over anhydrous sodium sulfate and evaporated under reduced pressure to remove the solvent to give a crude product. The crude product was triturated with ethyl acetate (30 mL) and filtered to give compound A1-1 (2.50 g, 8.30 mmol, yield 59.0%). LCMS (ESI) m z: 302.1 [M+H]$^+$, $^1$H NMR (400 MHz, CHLOROFORM-d) δ: 8.05 (s, 1H), 6.84-6.98 (m, 1H), 6.54-6.72 (m, 2H), 4.49-4.67 (m, 2H), 4.30-4.44 (m, 2H).

Step 2: Synthesis of Compound A1-2

Palladium hydroxide (615 mg, 438 μmol) was added to a solution of A1-1 (1.20 g, 3.98 mmol, 1.00 eq) in methanol (30 mL) at room temperature. The solution was degassed with hydrogen for three times, heated to 50° C. and stirred under 50 psi hydrogen for 2 hours. Then the reaction solution was cooled to room temperature and filtered to remove the catalyst. The filtrate was evaporated under reduced pressure to remove the solvent to give A1-2 (1.21 g, 3.99 mmol, yield 99.5%). $^1$H NMR (400 MHz, METHANOL-d$_4$) δ: 7.80 (s, 1H), 6.86 (d, J=4.4 Hz, 1H), 6.53 (d, J=4.4 Hz, 1H), 3.96-3.79 (m, 2H), 3.60-3.51 (m, 1H), 3.49-3.38 (m, 2H), 2.39-2.36 (m, 1H), 2.19-2.13 (m, 1H), 1.49 (d, J=3.6 Hz, 9H).

Step 3: Synthesis of Compound A1

Iodosuccinimide (26.7 g, 119 mmol, 3.00 eq) was added in batches to a solution of A1-2 (12.0 g, 39.6 mmol, 1.00 eq) in N,N-dimethylformamide (150 mL) at room temperature. The reaction solution was stirred at room temperature for 1 hour and then slowly added to ice water (200 mL). A solid was generated, and the mixture was filtrated to remove the solvent. The filter cake was dried by evaporation under reduced pressure to give compound A1, which was subjected to chiral resolution (column: IC (250 mm*50 mm, 10 m); mobile phase: [0.1% ammonia/ethanol]; B %: 30%-30%, min) to give compound A1-A (retention time 2.947 min, 3.00 g, 6.99 mmol, yield 17.7%) and compound A1-B (retention time 3.280 min, 3.00 g, 6.99 mmol, yield 17.7%).

Intermediate B1

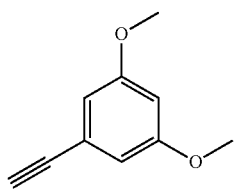

CAS: 1453211-48-7

Intermediate B2

Synthetic Route:

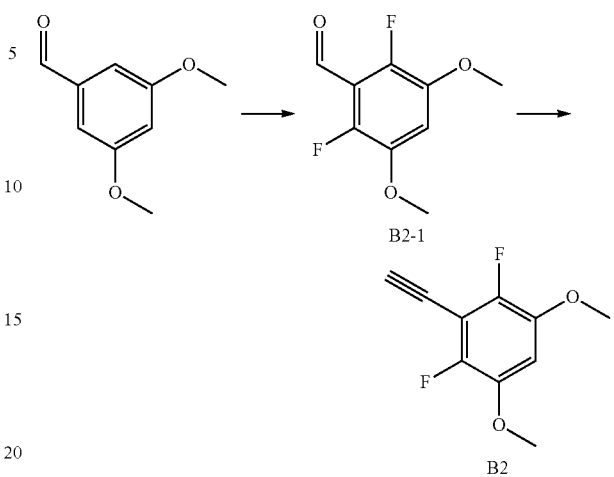

Step 1: Synthesis of Compound B2-1

1-Chloromethyl-4-fluoro-1,4-diazabicyclooctane bis(tetrafluoroborate) (512 g, 1.44 mol, 2.00 eq) was added in batches to a solution of 3,5-dimethoxybenzaldehyde (120 g, 722 mmol, 1.00 eq) in acetonitrile (3.50 L) at 0° C. The reaction solution was stirred at room temperature for 48 hours and then filtered. The filtrate was evaporated under reduced pressure to remove the solvent. The residue was diluted with 1 L ethyl acetate and washed with 2 L saturated aqueous sodium bicarbonate. The aqueous layer was extracted with ethyl acetate (600 mL) for three times. The organic layers were combined, washed with 2 L saturated brine, dried over anhydrous sodium sulfate and evaporated under reduced pressure to remove the solvent to give a crude product, which was purified by column chromatography (silica, from PE to PE/EA=3/1) to give compound B2-1 (45.5 g, 225 mmol, yield 31.2%). LCMS (ESI) m z: 203.0 [M+H]$^+$, $^1$H NMR (400 MHz, CHLOROFORM-d) δ: 10.29 (s, 1H), 6.84-6.80 (m, 1H), 3.84 (s, 6H).

Step 2: Synthesis of Compound B2

A mixture of 2,6-difluoro-3,5-dimethoxybenzaldehyde (8.30 g, 41.1 mmol, 1.00 eq), dimethyl (1-diazo-2-oxopropyl)phosphonate (9.5 g, 49.3 mmol, 1.20 eq) and potassium carbonate (11.4 g, 82.1 mmol, 2.00 eq) in 20 mL methanol was stirred at room temperature for 16 hours. The reaction solution was filtered. The filtrate was diluted with 50 mL dichloromethane, washed with 20 mL saturated aqueous sodium bicarbonate, dried over anhydrous sodium sulfate and filtered. The filtrate was evaporated under reduced pressure to remove the solvent to give compound B2 (3.50 g, 17.7 mmol, yield 43.0%). $^1$H NMR (400 MHz, CHLOROFORM-d) δ: 6.68-6.47 (m, 1H), 3.81 (s, 6H), 3.45 (s, 1H).

Intermediate B3

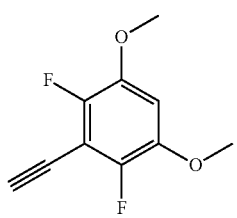

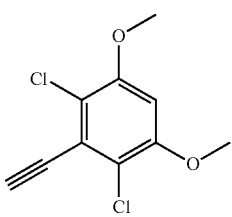

CAS: 1453211-48-7

Embodiment 1 and 2: Synthesis of Compound WX001A and WX001B

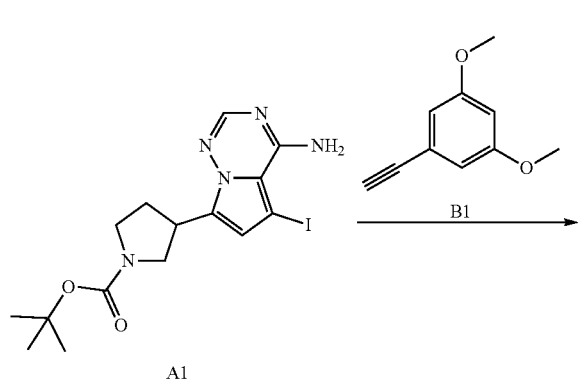

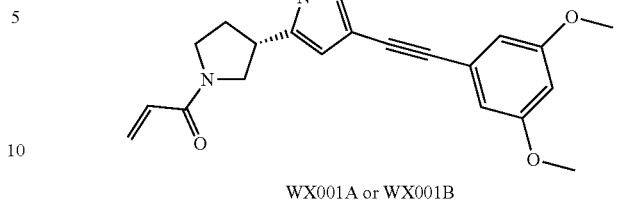

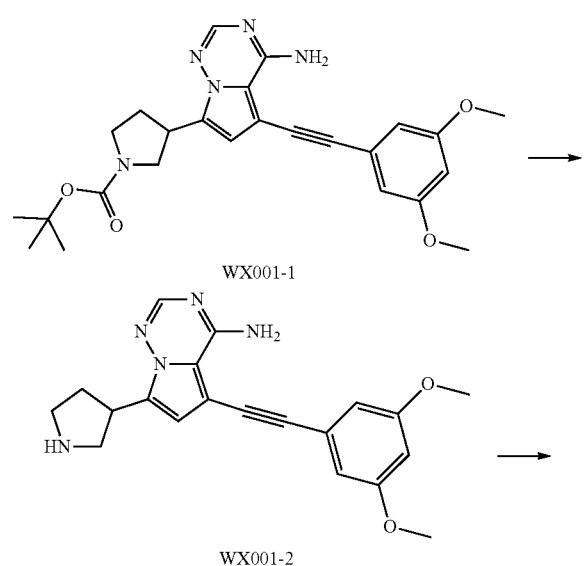

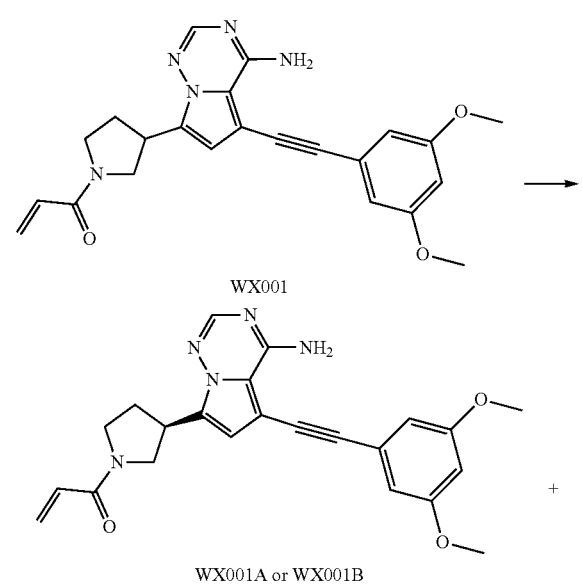

Step 1: Synthesis of Compound WX001-1

B1 (341 mg, 2.10 mmol, 1.50 eq), triethylamine (425 mg, 4.20 mmol, 582 μL, 3.00 eq) and 1'-bis(diphenylphosphino)ferrocene chloropalladium (102 mg, 140 mol, 0.10 eq) was added to a solution of A1 (600 mg, 1.40 mmol, 1.00 eq) in N,N-dimethylformamide (10 mL) at room temperature. The solution was degassed with nitrogen for three times, then heated to 90° C. and stirred for 1 hour. The reaction solution was cooled to room temperature, poured into 20 mL water and extracted with ethyl acetate (8 mL) for three times. The organic layers were combined, washed with saturated brine (15 mL), dried over anhydrous sodium sulfate and filtered. The filtrate was evaporated under reduced pressure to remove the solvent to give a crude product, which was purified by column chromatography (100-200 mesh silica, PE/EA=50/1 to 1/1) to give compound WX001-1 (390 mg, 841 μmol, yield 60.1%). LCMS (ESI) m z: 464.2 [M+H]$^+$, $^1$H NMR (400 MHz, CHLOROFORM-d) δ: 8.03 (s, 1H), 7.94 (s, 1H), 6.65 (d, J=2.0 Hz, 2H), 6.49-6.48 (m, 1H), 3.55-3.28 (m, 4H), 2.96 (s, 3H), 2.89 (s, 3H), 2.35-2.23 (m, 1H), 2.08-1.95 (m, 1H), 1.67-1.54 (m, 2H), 1.49 (s, 9H).

Step 2: Synthesis of Compound WX001-2

A solution of hydrogen chloride in ethyl acetate (4 M, 2.00 mL, 9.51 eq) was slowly added dropwise to a solution of WX001-1 (390 mg, 841 μmol, 1.00 eq) in ethyl acetate (2 mL) at room temperature. The solution was stirred for 1 hour and filtered to give a solid, which was dried under reduced pressure to give a hydrochloride of compound WX001-2 (200 mg, 500 μmol, yield 59.45%). LCMS (ESI) m z: 364.2 [M+H]$^+$, $^1$H NMR (400 MHz, METHANOL-d$_4$) δ: 8.13 (s, 1H), 7.11 (s, 1H), 6.79 (d, J=2.0 Hz, 2H), 6.61 (t, J=2.0 Hz, 1H), 4.18-4.07 (m, 1H), 3.91-3.79 (m, 7H), 3.68-3.55 (m, 1H), 3.52-3.41 (m, 2H), 2.67-2.55 (m, 1H), 2.40-2.28 (m, 1H).

Step 3: Synthesis of Compound WX001

Diisopropylethylamine (259 mg, 2.00 mmol, 349 μL, 4.00 eq) and a solution of acryloyl chloride in dichloromethane (0.25 M, 1.80 mL, 0.90 eq) were added to a suspension of WX001-2 hydrochloride (200 mg, 500 μmol, 1.00 eq) in dichloromethane (4.0 mL) at 0° C. The reaction solution was stirred for 5 minutes, then poured into 2 mL water and partitioned. The aqueous layer was extracted with dichloromethane. (1 mL) for three times. The organic layers were combined, dried over anhydrous sodium sulfate and filtered. The filtrate was evaporated under reduced pressure to remove the solvent to give a crude product, which was purified by preparative TLC plate (dichloromethane/methanol=10/1) to give compound WX001. Compound WX001 was subjected to chiral resolution (column: AS (250 mm*30 mm, 5 μm); mobile phase: [0.1% ammonia/ethanol]; B %: 40%-40%, min) to give WX001A (retention time 5.405 min, 65.0 mg, 156 μmol, yield 31.13%) and WX001B (retention time 5.802 min, 65.0 mg, 155 μmol, yield 31.13%).

WX001A: LCMS (ESI) m z: 418.1 [M+H]$^+$, $^1$HNMR (400 MHz, METHANOL-d$_4$) δ: 7.73 (d, J=3.2 Hz, 1H), 6.60-6.44 (m, 4H), 6.40-6.37 (m, 1H), 6.21-6.15 (m, 1H), 5.66-5.61 (m, 1H), 4.11-3.93 (m, 1H), 3.89-3.70 (m, 2H), 3.68 (s, 6H), 3.54-3.39 (m, 2H), 2.45-2.24 (m, 1H), 2.19-1.94 (m, 1H).

WX001B, LCMS (ESI) m z: 418.1 [M+H]$^+$, $^1$HNMR (400 MHz, METHANOL-d$_4$) δ: 7.88 (d, J=2.0 Hz, 1H), 6.75 (d, J=8.8 Hz, 1H), 6.70 (d, J=2.0 Hz, 2H), 6.68-6.59 (m, 1H), 6.54 (s, 1H), 6.41-6.18 (m, 1H), 5.87-5.65 (m, 1H), 4.27-4.06 (m, 1H), 4.05-3.91 (m, 1H), 3.90-3.83 (m, 1H), 3.82 (s, 6H), 3.79-3.69 (m, 1H), 3.67-3.55 (m, 1H), 2.58-2.40 (m, 1H), 2.36-2.13 (m, 1H).

Embodiment 3: Synthesis of Compound WX002A

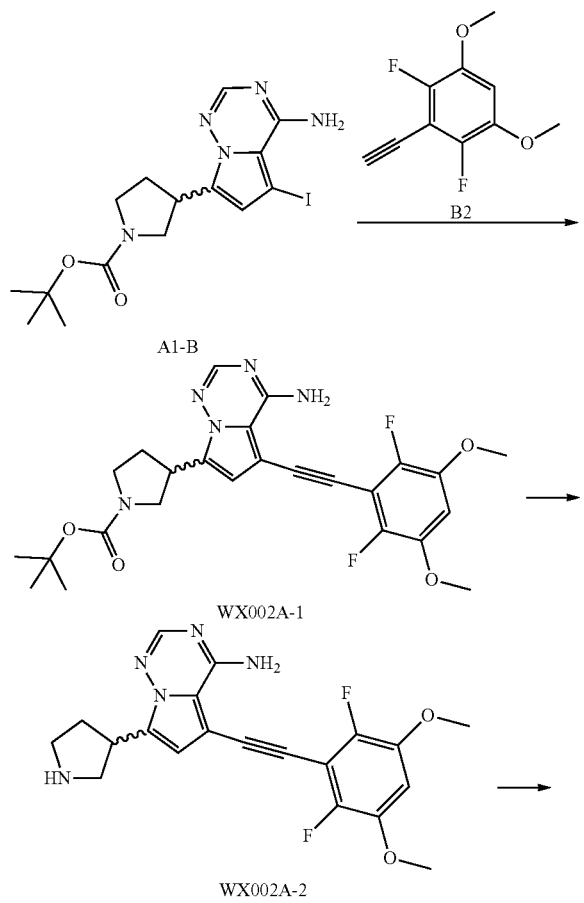

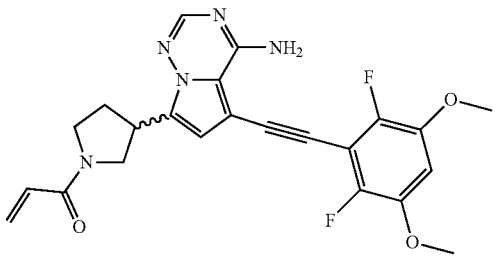

WX002A

Step 1: Synthesis of Compound WX002A-1

A solution of A1-B (900 mg, 2.10 mmol, 1.00 eq), B2 (623 mg, 3.14 mmol, 1.50 eq), triethylamine (636 mg, 6.29 mmol, 872 μL, 3.00 eq) and 1'-bis(diphenylphosphino)ferrocene chloropalladium (153 mg, 210 μmol, 0.10 eq) in 1.5 mL N,N-dimethylformamide was degassed with nitrogen and stirred at room temperature for 16 hours. Then the reaction solution was poured into 25 mL water and extracted with ethyl acetate (25 mL) for three times. The organic layers were combined, washed with 25 mL saturated brine, dried over anhydrous sodium sulfate and filtered. The filtrate was evaporated under reduced pressure to remove the solvent to give a crude product of WX002A-1 (850 mg).

Step 2 and step 3 was conducted according to the synthetic method of embodiment 1.

WX002A, LCMS (ESI) m z: 454.1 [M+H]$^+$, 476.1 [M+Na]$^+$, $^1$HNMR (400 MHz, CHLOROFORM-d) δ: 7.87 (d, J=2.0 Hz, 1H), 6.65 (d, J=7.2 Hz, 1H), 6.58-6.54 (m, 1H), 6.45-6.24 (m, 2H), 5.66-5.61 (m, 1H), 4.15-4.00 (m, 1H), 3.97-3.76 (m, 7H), 3.71-3.44 (m, 3H), 2.52-2.27 (m, 1H), 2.19-2.03 (m, 1H).

According to the methods of embodiments 1-3, the intermediates A1-A, A1-B and intermediates B2, B3 were used as raw materials to synthesize the compounds in the following table:

| Embodiment | Intermediate A | Intermediate B | Structure | Compound |
|---|---|---|---|---|
| 4 | A1-A | B2 | 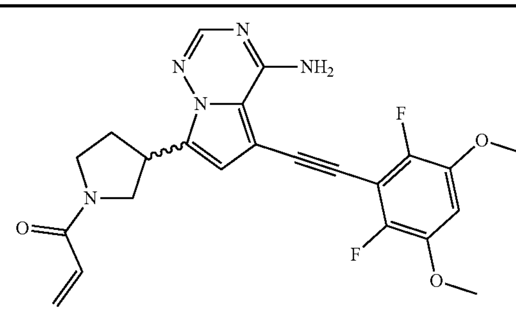 | WX002B |

-continued

| Embodiment | Intermediate A | Intermediate B | Structure | Compound |
|---|---|---|---|---|
| 5 | A1-B | B3 | 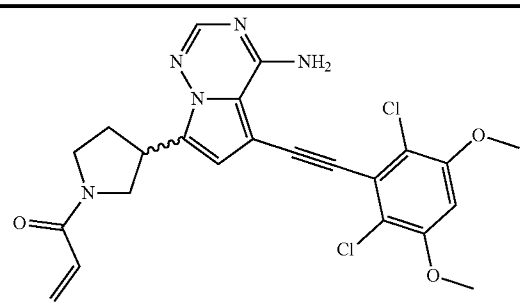 | WX003A |
| 6 | A1-A | B3 | 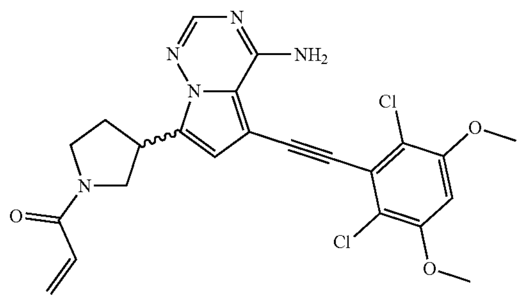 [SMILES: C=CC(=O)N1CCC(c2cc(C#Cc3c(Cl)c(OC)cc(OC)c3Cl)c3c(N)ncnn23)C1] | WX003B |

NMR and MS data:

| Embodiment | Compound | NMR | MS m/z: |
|---|---|---|---|
| 1 | WX001A | $^1$H NMR (400 MHz, METHANOL-$d_4$) δ: 7.73 (d, J = 3.2 Hz, 1H), 6.60-6.44 (m, 4H), 6.40-6.37 (m, 1H), 6.21-6.15 (m, 1H), 5.66-5.61 (m, 1H), 4.11-3.93 (m, 1H), 3.89-3.70 (m, 2H), 3.68 (s, 6H), 3.54-3.39 (m, 2H), 2.45-2.24 (m, 1H), 2.19-1.94 (m, 1H) | 418.1 |
| 2 | WX001B | $^1$H NMR (400 MHz, METHANOL-$d_4$) δ: 7.88 (d, J = 2.0 Hz, 1H), 6.75 (d, J = 8.8 Hz, 1H), 6.70 (d, J = 2.0 Hz, 2H), 6.68-6.59 (m, 1H), 6.54 (s, 1H), 6.41-6.18 (m, 1H), 5.87-5.65 (m, 1H), 4.27-4.06 (m, 1H), 4.05-3.91 (m, 1H), 3.90-3.83 (m, 1H), 3.82 (s, 6H), 3.79-3.69 (m, 1H), 3.67-3.55 (m, 1H), 2.58-2.40 (m, 1H), 2.36-2.13 (m, 1H) | 418.1 |
| 3 | WX002A | $^1$H NMR (400 MHz, CHLOROFORM-d) δ: 7.87 (d, J = 2.0 Hz, 1H), 6.65 (d, J = 7.2 Hz, 1H), 6.58-6.54 (m, 1H), 6.45-6.24 (m, 2H), 5.66-5.61 (m, 1H), 4.15-4.00 (m, 1H), 3.97-3.76 (m, 7H), 3.71-3.44 (m, 3H), 2.52-2.27 (m, 1H), 2.19-2.03 (m, 1H) | 454.1, 476.1 |
| 4 | WX002B | $^1$H NMR (400 MHz, CHLOROFORM-d) δ: 7.87 (d, J = 2.0 Hz, 1H), 6.65 (d, J = 7.2 Hz, 1H), 6.58-6.54 (m, 1H), 6.46-6.28 (m, 2H), 5.76-5.53 (m, 1H), 4.16-3.99 (m, 1H), 3.97-3.75 (m, 7H), 3.72-3.45 (m, 3H), 2.52-2.28 (m, 1H), 2.20-2.04 (m, 1H) | 454.1 |
| 5 | WX003A | $^1$H NMR (400 MHz, CHLOROFORM-d) δ: 7.88 (d, J = 1.6 Hz, 1H), 6.68 (d, J = 4.8 Hz, 1H), 6.49 (d, J = 2.0 Hz, 1H), 6.29-6.47 (m, 2H), 5.57-5.72 (m, 1H), 4.03-4.15 (m, 1H), 3.79-3.99 (m, 8H), 3.52-3.69 (m, 2H), 2.29-2.52 (m, 1H), 2.04-2.18 (m, 1H) | 487.8, 507.9 |
| 6 | WX003B | $^1$H NMR (400 MHz, CHLOROFORM-d) δ: 7.89 (d, J = 1.6 Hz, 1H), 6.68 (d,J = 4.8 Hz, 1H), 6.49 (d,J = 1.6 Hz, 1H), 6.32-6.43 (m, 2H), 5.66-5.61 (m, 1H), 4.03-4.15 (m, 1H), 3.76-3.97 (m, 8H), 3.56-3.71 (m, 2H), 2.30-2.52 (m, 1H), 2.05-2.19 (m, 1H) | 488.0, 508.1 |

Effect Embodiment 1: In Vitro Assay

The IC$_{50}$ value was determined by $^{33}$P isotope-labeled kinase activity assay (Reaction Biology Corp) to evaluate the inhibitory activity of the test compounds on human FGFR1 and FGFR4.

Buffer: 20 mM Hepes (pH 7.5), 10 mM MgCl$_2$, 1 mM EGTA, 0.02% Brij35, 0.02 mg/mL BSA, 0.1 mM Na$_3$VO$_4$, 2 mM DTT, 1% DMSO.

Test procedure: the test compound was dissolved in DMSO at room temperature to prepare a 10 mM solution for use. The substrate was dissolved in a freshly prepared buffer, followed by addition of the kinase to be tested and the resulting mixture was thoroughly mixed. The solution of the test compound in DMSO was added to the above reaction solution by acoustic technique (Echo 550). The concentration of the compound in the reaction solution was 10 μM, 3.33 μM, 1.11 μM, 0.370 μM, 0.123 μM, 41.2 nM, 13.7 nM, 4.57 nM, 1.52 nM, 0.508 nM, or 10 M, 2.50 M, 0.62 M, 0.156 M, 39.1 nM, 9.8 nM, 2.4 nM, 0.61 nM, 0.15 nM, 0.038 nM. After incubation for 15 minutes, $^{33}$P-ATP (activity 0.01 μCi/μL, corresponding concentration was listed in table 1) was added to initiate the reaction. The supplier, lot number, and concentration of FGFR1, FGFR4 and substrate in the reaction solution were listed in table 1. The reaction was allowed to proceed at room temperature for 120 minutes, then the reaction solution was spotted on P81 ion exchange filter paper (Whatman #3698-915). After the filter paper was washed with 0.75% phosphoric acid solution, the radioactivity of the remained phosphorylated substrate on the filter paper was determined. The kinase activity data was expressed as a ratio of the kinase activity of the test compound to the kinase activity of the control group (DMSO), and the IC$_{50}$ value was obtained by curve fitting using Prism4 software (GraphPad). The experimental results were shown in Table 2.

TABLE 1 information of kinase, substrate and ATP in the in vitro assays

| Kinase | Suppler | Cat # | Lot # | Concentration of Kinase in the reaction solution (nM) | Substrate | Suppler | Cat # | Lot # | Concentration of substrate in reaction solution (mg/mL) | Concentration of ATP (μM) |
|---|---|---|---|---|---|---|---|---|---|---|
| FGFR4 | Invitrogen | P3054 | 26967J | 2.5 | pEY (mg/mL) + Mn | Sigma | P7244-250MG | 062K5104V | 0.2 | 100 |
| FGFR1 | Invitrogen | PV3146 | 28427Q | 1.75 | pEY (mg/mL) + Mn | Sigma | P7244-250MG | 062K5104V | 0.2 | 5 |

TABLE 2 in vitro screening test results of the compound of the invention

| | IC$_{50}$ (nM) | | Inhibition activity difference (IC$_{50}$ ratio) |
|---|---|---|---|
| Compound | FGFR1 | FGFR4 | FGFR4/FGFR1 |
| Reference embodiment 1 | 0.6 | 3.0 | 5 |
| Embodiment 1 | 18.3 | 125 | 7 |
| Embodiment 2 | 0.04 | 0.27 | 7 |
| Embodiment 3 | 0.7 | 6.6 | 9 |
| Embodiment 4 | 0.07 | 0.08 | 1 |
| Embodiment 5 | 21.8 | 450 | 21 |
| Embodiment 6 | 0.3 | 4.6 | 15 |

Conclusion: some compounds of the invention exhibit picomolar-level inhibitory activity on FGFR, and some compounds exhibit comparable inhibitory activity on FGFR4 and FGFR1.

Conclusion: some compounds of the invention exhibit picomolar-level inhibitory activity on FGFR, and some compounds exhibit comparable inhibitory activity on FGFR4 and FGFR1.

What is claimed is:

1. A compound of formula (I):

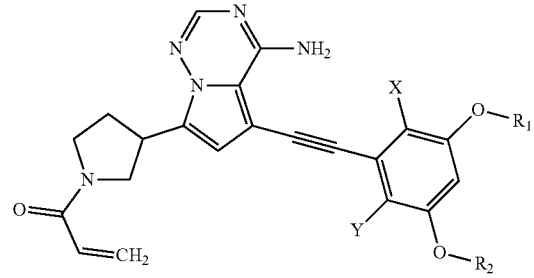

or a pharmaceutically acceptable salt or stereoisomer thereof, wherein:

R$_1$ is C$_{1-3}$ alkyl;
R$_2$ is C$_{1-3}$ alkyl;
X is H, F, Cl, Br, or I; and
Y is H, F, Cl, Br, or I.

2. The compound of claim 1, or a pharmaceutically acceptable salt or stereoisomer thereof, wherein R$_1$ is CH$_3$ or CH$_2$CH$_3$.

3. The compound of claim 1, or a pharmaceutically acceptable salt or stereoisomer thereof, wherein R$_2$ is CH$_3$ or CH$_2$CH$_3$.

4. The compound of claim 1, or a pharmaceutically acceptable salt or stereoisomer thereof, wherein:
X is H; and
Y is H.

5. The compound of claim 1, or a pharmaceutically acceptable salt or stereoisomer thereof, wherein:
X is F; and
Y is F.

6. The compound of claim 1, or a pharmaceutically acceptable salt or stereoisomer thereof, wherein:
X is Cl; and
Y is Cl.

7. The compound of claim 2, or a pharmaceutically acceptable salt or stereoisomer thereof, wherein R$_2$ is CH$_3$ or CH$_2$CH$_3$.

8. The compound of claim 7, or a pharmaceutically acceptable salt or stereoisomer thereof, wherein:
X is H; and
Y is H.

9. The compound of claim 7, or a pharmaceutically acceptable salt or stereoisomer thereof, wherein:
X is F; and
Y is F.

10. The compound of claim 7, or a pharmaceutically acceptable salt or stereoisomer thereof, wherein:

X is Cl; and

Y is Cl.

11. The compound of claim 1, or a stereoisomer thereof, wherein the stereoisomer of the compound is of formula (I-1) or formula (I-2):

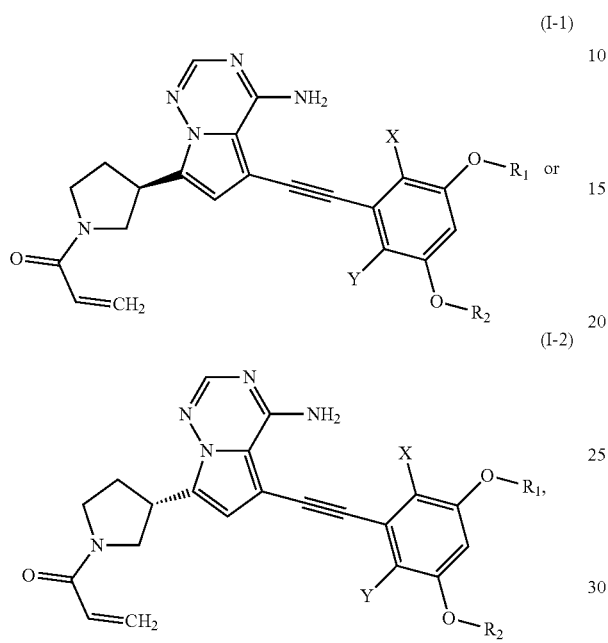

or a pharmaceutically acceptable salt thereof.

12. A pharmaceutical composition comprising a pharmaceutically acceptable carrier and a therapeutically effective amount of the compound of claim 1, or a pharmaceutically acceptable salt or stereoisomer thereof.

13. A method for inhibiting fibroblast growth factor receptor activity in a subject in need thereof, comprising administering to the subject a therapeutically effective amount of the compound of claim 1, or a pharmaceutically acceptable salt or stereoisomer thereof.

14. The method of claim 13, wherein the subject has a disease caused by fibroblast growth factor receptor mutation or overexpression.

15. The method of claim 14, wherein the disease caused by fibroblast growth factor receptor mutation or overexpression is selected from the group consisting of a solid tumor, gastric cancer, hepatocellular carcinoma, and intrahepatic cholangiocarcinoma.

16. A method for inhibiting fibroblast growth factor receptor activity in a subject in need thereof, comprising administering to the subject a therapeutically effective amount of the pharmaceutical composition of claim 12.

17. The method of claim 16, wherein the subject has a disease caused by fibroblast growth factor receptor mutation or overexpression.

18. The method of claim 17, wherein the disease caused by fibroblast growth factor receptor mutation or overexpression is selected from the group consisting of a solid tumor, gastric cancer, hepatocellular carcinoma, and intrahepatic cholangiocarcinoma.

19. A compound, or stereoisomer thereof, wherein the stereoisomer of the compound is selected from the group consisting of:

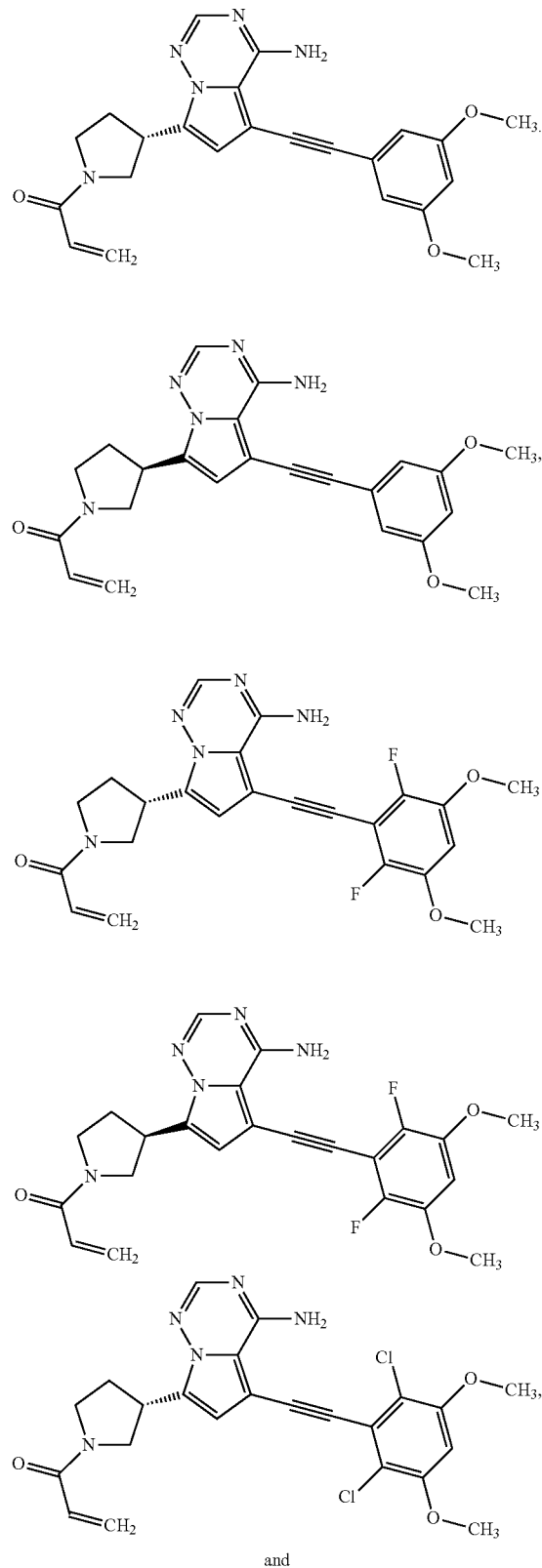

and

-continued
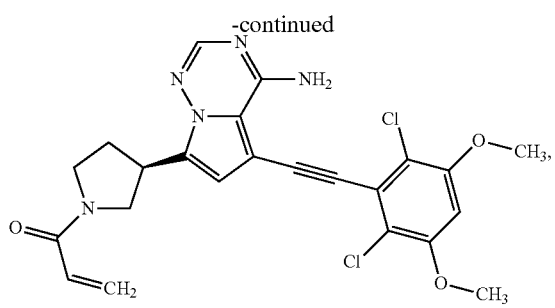
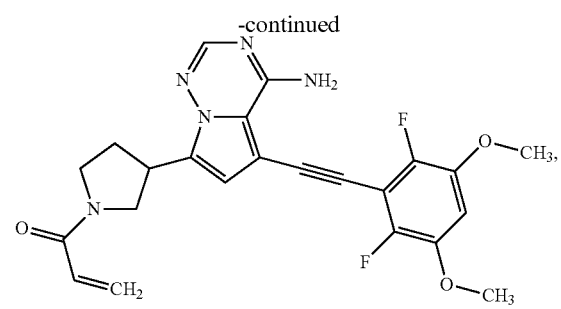
or a pharmaceutically acceptable salt thereof.
20. A compound selected from the group consisting of:
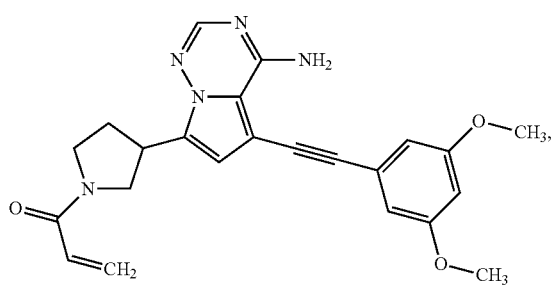
and
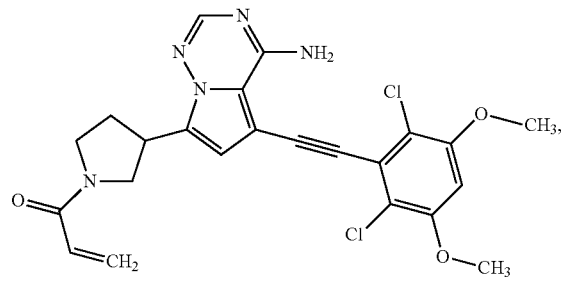
or a pharmaceutically acceptable salt or stereoisomer thereof.
* * * * *